(12) United States Patent
Ishikawa et al.

(10) Patent No.: US 11,302,007 B2
(45) Date of Patent: Apr. 12, 2022

(54) IMAGE PROCESSING APPARATUS, IMAGE PROCESSING METHOD, IMAGE PROCESSING SYSTEM, AND STORAGE MEDIUM

(71) Applicant: CANON KABUSHIKI KAISHA, Tokyo (JP)

(72) Inventors: Ryo Ishikawa, Kawasaki (JP); Toru Tanaka, Funabashi (JP)

(73) Assignee: Canon Kabushiki Kaisha, Tokyo (JP)

( * ) Notice: Subject to any disclaimer, the term of this patent is extended or adjusted under 35 U.S.C. 154(b) by 39 days.

(21) Appl. No.: 16/749,894

(22) Filed: Jan. 22, 2020

(65) Prior Publication Data
US 2020/0160526 A1 May 21, 2020

Related U.S. Application Data

(63) Continuation of application No. PCT/JP2018/027609, filed on Jul. 24, 2018.

(30) Foreign Application Priority Data
Aug. 3, 2017 (JP) .............................. JP2017-150877

(51) Int. Cl.
 *G06T 7/00* (2017.01)
 *G06T 3/40* (2006.01)
 *G06T 5/50* (2006.01)

(52) U.S. Cl.
CPC .......... *G06T 7/0016* (2013.01); *G06T 3/4007* (2013.01); *G06T 5/50* (2013.01); *G06T 2207/10081* (2013.01)

(58) Field of Classification Search
CPC ....... G06T 7/0016; G06T 3/4007; G06T 5/50; G06T 2207/10081; G06T 2207/20224;
(Continued)

(56) References Cited

U.S. PATENT DOCUMENTS

| 2001/0021263 A1 | 9/2001 | Oosawa |
| 2008/0193005 A1 | 8/2008 | Seghers |

(Continued)

FOREIGN PATENT DOCUMENTS

| EP | 2312531 A1 | 4/2011 |
| JP | 2006-223739 A | 8/2006 |

(Continued)

OTHER PUBLICATIONS

Machine translation for WO 2005-009242, IDS (Year: 2005).*
(Continued)

*Primary Examiner* — Qian Yang
(74) *Attorney, Agent, or Firm* — Canon U.S.A., Inc. IP Division

(57) ABSTRACT

An apparatus that can obtain a subtraction image efficiently is provided. An image processing apparatus obtains a target image constituted by a set of voxels arranged in a discretized manner; sets a search area in the target image; and obtains, in a partial area included in the search area, on the basis of at least one of a voxel value included in the partial area and an interpolated value obtained by interpolation of a voxel of the target image, at least one of a maximum and a minimum of a voxel value and an interpolated value within the search area.

17 Claims, 11 Drawing Sheets

(58) Field of Classification Search
CPC ....... G06T 2200/04; G06T 2207/10072; G06T 5/001; A61B 6/00
See application file for complete search history.

(56) References Cited

U.S. PATENT DOCUMENTS

2009/0074276 A1   3/2009  Doi
2011/0075900 A1   3/2011  Masumoto
2013/0058556 A1   3/2013  Ohishi
2017/0178307 A1   6/2017  Yan

FOREIGN PATENT DOCUMENTS

JP        2011-92685 A    5/2011
WO     2005/009242 A1   2/2005
WO     2013/031718 A1   3/2013

OTHER PUBLICATIONS

Yoshinori Itai, et al., "Development of a voxel-matching technique for substantial reduction of subtraction artifacts in temporal subtraction images obtained from thoracic MDCT", Journal of digital imaging, vol. 23, No. 1, pp. 31-38, Feb. 2010.

\* cited by examiner

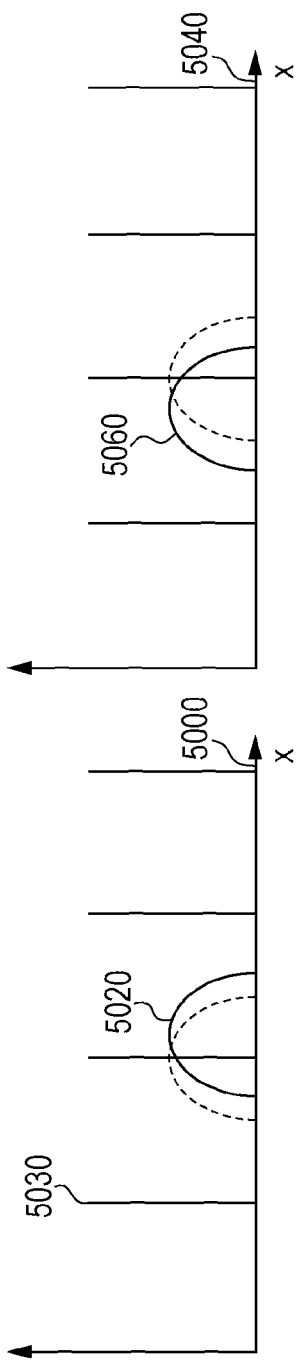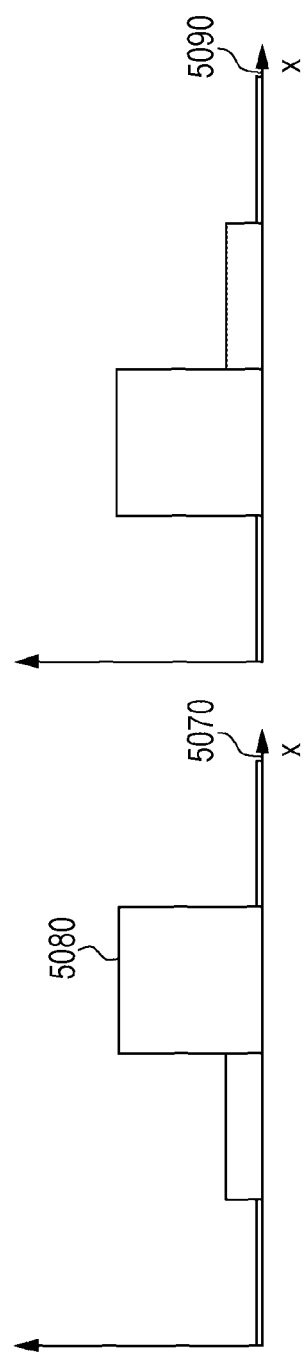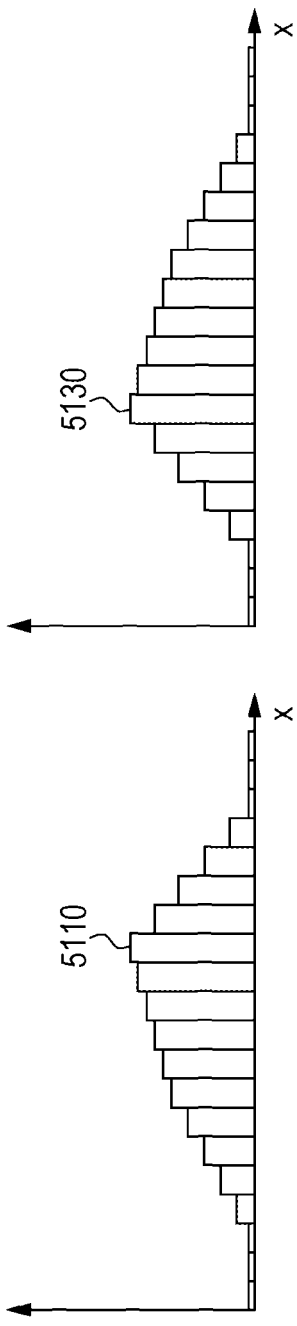

IMAGE PROCESSING APPARATUS, IMAGE PROCESSING METHOD, IMAGE PROCESSING SYSTEM, AND STORAGE MEDIUM

CROSS-REFERENCE TO RELATED APPLICATIONS

This application is a Continuation of International Patent Application No. PCT/JP2018/027609, filed Jul. 24, 2018, which claims the benefit of Japanese Patent Application No. 2017-150877, filed Aug. 3, 2017, both of which are hereby incorporated by reference herein in their entirety.

TECHNICAL FIELD

The disclosure herein relates to an image processing apparatus, an image processing method, an image processing system, and a storage medium.

BACKGROUND ART

In the medical field, physicians make a diagnosis by using medical images that are captured with various modalities. In particular, for follow-up care of the state of a subject, a physician compares a plurality of images that are captured with the same modality at different times to observe a temporal change of the subject. In the fields other than the medical field, also, in a case where a temporal change of an object is observed, substantially the same work may be carried out. In addition to the temporal comparison, two images of the same subject captured under different contrast conditions or different imaging parameters may be compared for diagnosis. Note that one of the images to be compared will be referred to as a first image, and the other of the images will be referred to as a second image in the following description.

An image subtraction technique is known for assisting comparison between images by registration between the first image and the second image and displaying a subtraction image in which a difference between the images is visualized. There is, however, an issue in that noise is generated in the subtraction image due to an error in registration or a difference between intensities at the same site in the images. As a solution to such an issue, NPL 1 discloses the following technique (voxel-matching method). In this technique, differences between a voxel of interest in the first image and a corresponding voxel and voxels near the corresponding voxel in the second image are obtained, and the minimum value among the differences is set as an intensity in a subtraction image. According to this, since a difference value between the voxel of interest and voxels having the closest luminance from the neighborhood of the corresponding voxel is employed, noise in the subtraction image can be reduced.

CITATION LIST

Non Patent Literature

NPL 1 Yoshinori Itai, Hyoungseop Kim, Seiji Ishikawa, Shigehiko Katsuragawa, Kunio Doi, "Development of a voxel-matching technique for substantial reduction of subtraction artifacts in temporal subtraction images obtained from thoracic MDCT." Journal of digital imaging, vol. 23, No. 1, pp. 31-38, 2010.

However, there is an issue in order to perform more efficient calculation for obtaining the voxel having the closest luminance from the neighborhood of the corresponding voxel.

SUMMARY OF INVENTION

An image processing apparatus according to an embodiment of the present invention includes first obtaining means for obtaining a target image constituted by a set of voxels arranged in a discretized manner; setting means for setting a search area in the target image; and second obtaining means for obtaining, in a partial area included in the search area, on the basis of at least one of a voxel value included in the partial area and an interpolated value obtained by interpolation of a voxel of the target image, at least one of a maximum and a minimum of a voxel value and an interpolated value within the search area.

Further features of the present invention will become apparent from the following description of exemplary embodiments with reference to the attached drawings.

BRIEF DESCRIPTION OF DRAWINGS

FIG. 11A is a diagram for describing processing in the embodiment of the present invention.

FIG. 11B is a diagram for describing processing in the embodiment of the present invention.

FIG. 11C is a diagram for describing processing in the embodiment of the present invention.

DESCRIPTION OF EMBODIMENTS

Figure 1:
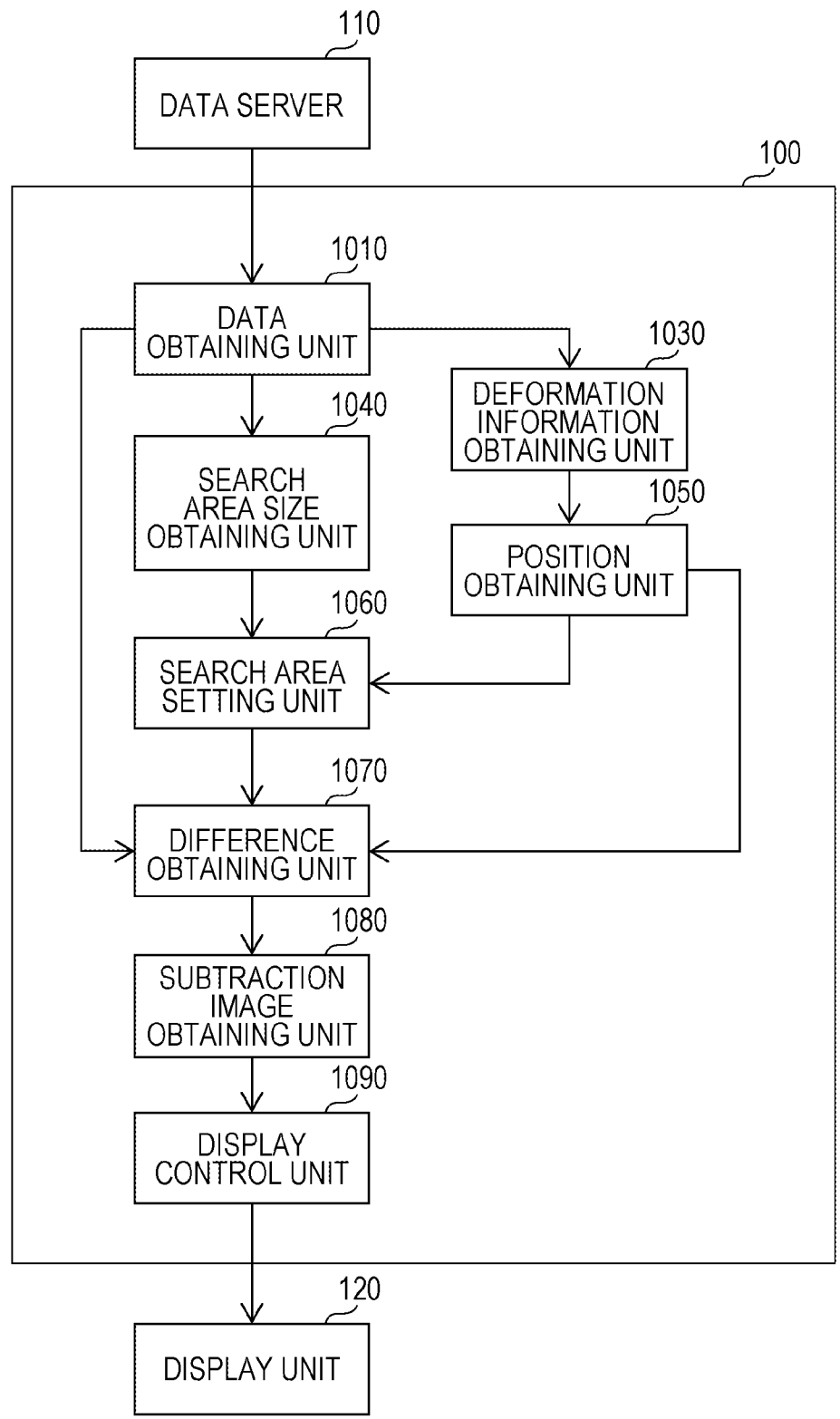
FIG. 1 is a diagram illustrating an example of a functional configuration of an image processing apparatus according to a first embodiment.

Now, embodiments of the present invention will be described with reference to the drawings. Note that the scope of the invention is not limited to the illustrated examples.

First Embodiment

An image processing apparatus according to this embodiment is an apparatus that obtains a three-dimensional subtraction image between a plurality of three-dimensional images (first image and second image). In order to obtain a difference of a particular part between the images, the image processing apparatus according to this embodiment obtains a position of interest in the first image (reference image) and a corresponding position in the second image (target image) corresponding thereto, and sets a target area on the basis of the corresponding position. For example, in the second image, a search area centered at the corresponding position is set. At this time, by using a shift of position of a voxel, at which an original image pickup signal is most reflected, due to a shift of discretization position between compared images, by half a voxel size at most, the size of the search area is obtained on the basis of the voxel size of each of the first image and the second image. Then, through a comparison operation between an intensity at the position of interest in the first image and an intensity at the plurality of voxels within the search area that is set in the neighborhood of the corresponding position in the second image, a comparison value is obtained. Specifically, a difference value is obtained through a subtraction operation between the above intensities. Then, a three-dimensional subtraction image is obtained, and that value is the intensity at the position of interest in the three-dimensional subtraction image. Thus, by obtaining difference values from the search area having a minimum necessary size, a user can observe a three-dimensional subtraction image in which noise due to a shift of discretization position is reduced by leaving as many signals as possible necessary for diagnosis of a difference due to a temporal change, for example.

A three-dimensional image (medical image) used by an image processing apparatus 100 for obtaining the subtraction image is, for example, an image captured with any of modalities such as a diagnostic magnetic resonance imaging apparatus, a diagnostic ultrasound imaging apparatus, a photoacoustic imaging apparatus, a diagnostic computer tomography imaging apparatus, and a diagnostic positron emission tomography imaging apparatus. In recent years, including medical images obtained with the above various modalities, a medical image used for diagnosis and various types of information regarding diagnosis have been digitized. For information communication between an imaging apparatus and any of various types of apparatuses that is connected to the imaging apparatus, for example, the digital imaging and communications in medicine (DICOM) standard is often used. DICOM is a standard that defines medical image formats and communication protocols between apparatuses handling these images. Images treated based on DICOM are constituted by meta data and image data. The meta data includes information regarding patient, examination, series, and image, for example. The meta data is constituted by an aggregation of data elements called DICOM data elements. A tug is added to each of the DICOM data elements for identifying the data element. For example, a tug indicating that the data is image data is added to image data, which is voxel data, as a DICOM data element. In this embodiment, processing performed by the image processing apparatus 100 and three-dimensional images (medical images) used by the image processing apparatus 100 may comply with DICOM. In addition, the image processing apparatus 100 may obtain information necessary for various types of processing from information included in meta data of a three-dimensional image (medical image) or may obtain the information by making an inquiry to an external apparatus based on DICOM.

Figure 10:
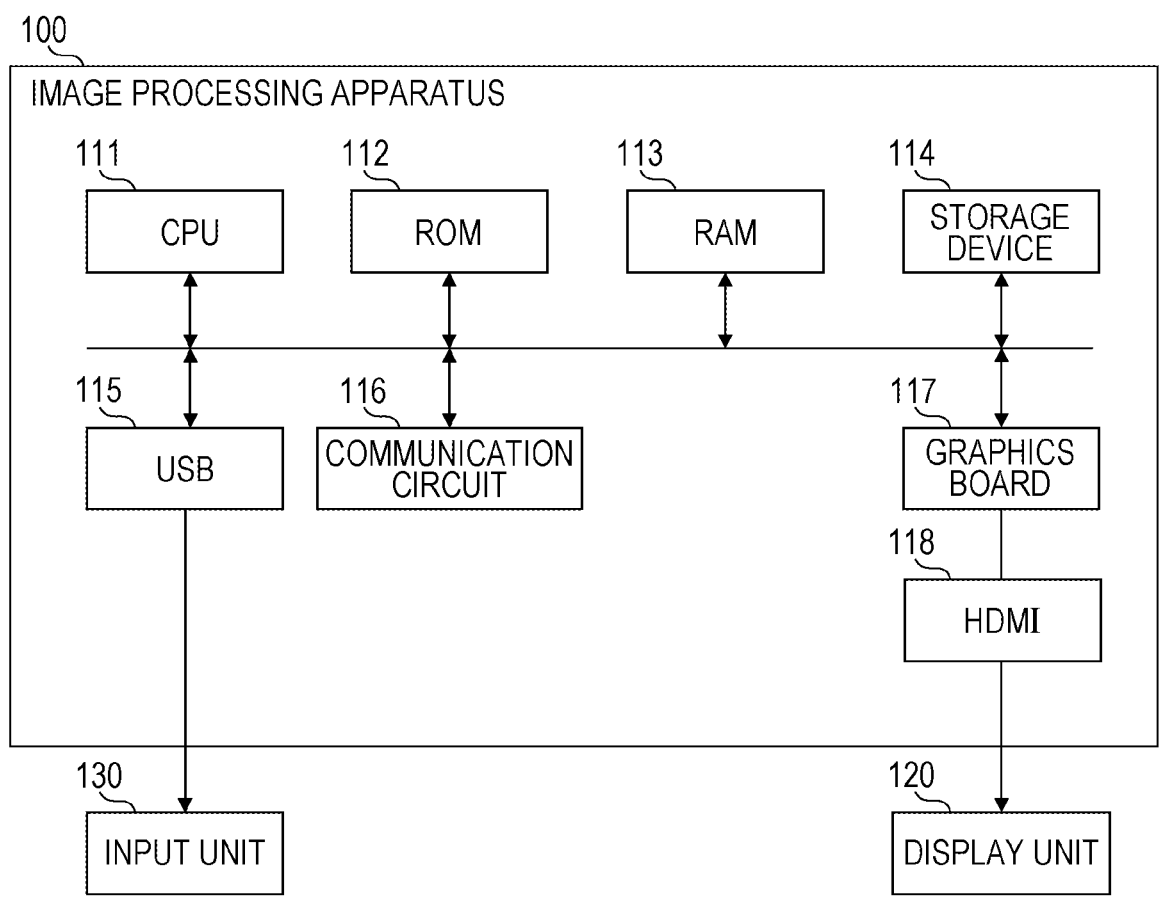
FIG. 10 is a diagram illustrating an example of a hardware configuration of an image processing apparatus according to an embodiment of the present invention.

FIG. 10 is a diagram illustrating an example of a hardware configuration of the image processing apparatus 100 according to an embodiment of the present invention. The image processing apparatus 100 is a computer, for example. The image processing apparatus 100 includes a CPU 111, a ROM 112, a RAM 113, a storage device 114, a USB 115, a communication circuit 116, and a graphics board 117. These are connected via a bus so that communication can be performed. The bus is used for transmitting/receiving data between hardware components that are connected or for transmitting a command from the CPU 111 to another hardware component.

The central processing unit (CPU) 111 is a control circuit that generally controls the image processing apparatus 100 and the units connected thereto. The CPU 111 performs control by executing a program stored in the ROM 112. In addition, the CPU 111 executes a display driver that is software for controlling a display unit 120 and performs display control of the display unit 120. Furthermore, the CPU 111 performs input/output control of an input unit 130.

The read only memory (ROM) 112 stores programs that store a control procedure of the CPU 111 and data. The ROM 112 stores a boot program or various initial data items of the image processing apparatus 100. In addition, the ROM 112 stores various programs for implementing processing of the image processing apparatus 100.

The random access memory (RAM) 113 provides a storage area for work when the CPU 111 performs control with a command program. The RAM 113 includes a stack and a work area. The RAM 113 stores a program for executing processing in the image processing apparatus 100 and the units connected thereto and various parameters used for image processing. The RAM 113 stores a control program executed by the CPU 111 and temporarily stores various data items for the CPU 111 to perform various types of control.

The storage device 114 is an auxiliary storage device that stores various data items such as the first image and the second image, which will be described later. The storage device 114 is, for example, a hard disk drive (HDD) or a solid state drive (SSD).

The universal serial bus (USB) 115 is a connection unit connected to the input unit 130.

The communication circuit 116 is a circuit for performing communication with various types of external apparatus connected to a communication network. The communication circuit 116, for example, stores information to be output in a transfer packet and outputs the information to an external apparatus via the communication network by a communication technique such as TCP/IP. The image processing apparatus 100 may include a plurality of communication circuits in accordance with a desired communication mode.

The graphics board 117 includes a graphics processing unit (CPU) and a video memory. The GPU, for example, performs operation related to reconstruction processing for generating a photoacoustic image from a photoacoustic signal.

A high definition multimedia interface (HDMI) (registered trademark) 118 is a connection unit connected to the display unit 120.

The CPU 111 and the GPU are examples of processors. In addition, the ROM 112, the RAM 113, and the storage device 114 are examples of memories. The image processing apparatus 100 may include a plurality of processors. In the first embodiment, a processor of the image processing apparatus 100 executes a program stored in a memory, and thereby the function of each unit of the image processing apparatus 100 is implemented.

In addition, the image processing apparatus 100 may include a CPU, a CPU, or an application specific integrated circuit (ASIC) that specifically perform specific processing. The image processing apparatus 100 may include a field-programmable gate array (FPGA) in which specific processing or all processing is programmed. Hereinafter, a processor includes a configuration that operates and controls processing related to the embodiment of the present invention alone. In addition, the processor includes at least one configuration that operates and controls processing related to the embodiment of the present invention in a dispersed manner. In this light, the ASIC and FPGA are examples of processors.

FIG. 1 illustrates the configuration of an image diagnosis system according to this embodiment. As illustrated in FIG. 1, the image processing apparatus 100 in this embodiment is connected to a data server 110 and the display unit 120.

The data server 110 holds a first image and a second image that are designated by a user as targets from which a subtraction image is to be obtained. The first image and the second image are three-dimensional tomographic images (volume data) obtained by imaging a subject in advance with the same modality and under different conditions (e.g., date and time, contrast conditions, imaging parameters). The modality that images the three-dimensional tomographic images may be an MRI apparatus, an X-ray CT apparatus, a three-dimensional ultrasound imaging apparatus, a photoacoustic tomography apparatus, a PET/SPECT, an OCT apparatus, and the like. In addition, the first image and the second image may be images obtained by imaging the same patient for follow-up care with the same modality and the same positioning at different times and dates or may be images obtained by imaging the same patient under different contrast conditions and different imaging parameters. In addition, the first image and the second image may be images obtained by imaging different patients or may be a patient's image and a standard image. The first image and the second image are input to the image processing apparatus 100 through a data obtaining unit 1010.

The display unit 120 is a monitor that displays an image that the image processing apparatus 100 obtains.

The image processing apparatus 100 is constituted by the following components. The data obtaining unit 1010 obtains the first image and the second image that are input to the image processing apparatus 100. The data obtaining unit 1010 is an example of first obtaining means. A deformation information obtaining unit 1030 obtains deformation information representing a correspondence relationship of positions in images that are the first image and the second image. That is, the deformation information obtaining unit 1030 obtains information regarding deformation for registration between the first image and the second image. A search area size obtaining unit 1040 obtains a search area size on the basis of the voxel size of each of the first image and the second image. A position obtaining unit 1050 obtains the position of interest in the first image, and by using the deformation information obtained by the deformation information obtaining unit 1030, obtains the corresponding position in the second image corresponding to the position of interest in the first image. A search area setting unit 1060 sets the search area having the search area size in the neighborhood of the corresponding position in the second image. A difference obtaining unit 1070 obtains a comparison value through a comparison operation between an intensity at a voxel of interest in the first image and an intensity within the search area in the second image. More specifically, the difference obtaining unit 1070 obtains a difference value at the position of interest through a comparison operation between at least one of a maximum and a minimum of the intensity within the search area and the intensity at the position of interest in the first image. In this light, the difference obtaining unit 1070 is an example of third obtaining means. A subtraction image obtaining unit 1080 obtains a subtraction image in which the obtained difference value is the intensity at the position of interest. A display control unit 1090 performs display control to cause the display unit 120 to arrange the first image, the second image, and the subtraction image for display.

Figure 2:
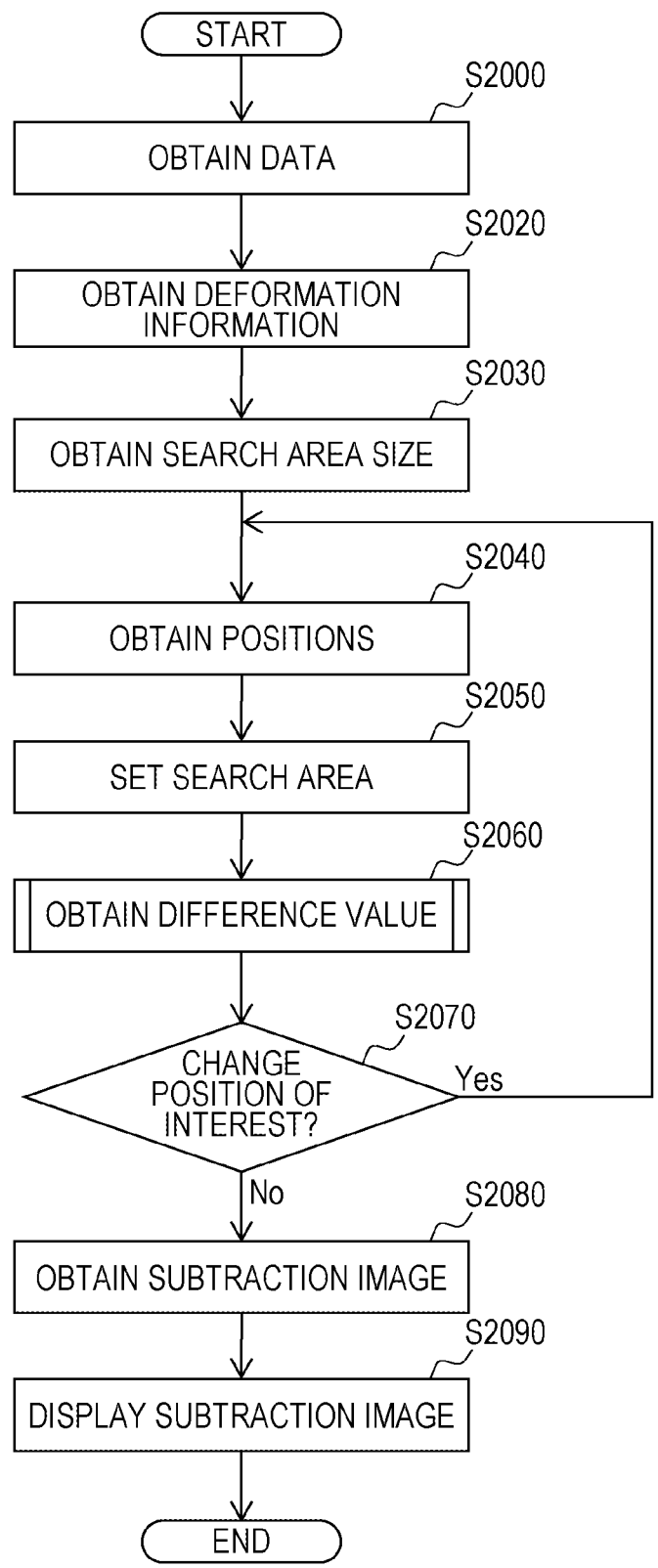
FIG. 2 is a flowchart illustrating an example of an entire processing procedure in the first embodiment.

FIG. 2 illustrates a flowchart of an entire processing procedure performed by the image processing apparatus 100.

S2000: Obtain Data

In step S2000, the data obtaining unit 1010 obtains the first image and the second image that are input to the image processing apparatus 100. Then, the data obtaining unit 1010 outputs the obtained first image and second image to the deformation information obtaining unit 1030. Each of the first image and the second image in this embodiment is a three-dimensional image and a set of voxels that are aligned at equal intervals in every direction of the three-dimensional coordinate axes. The interval between voxels (hereinafter also referred to as voxel size) of the first image in this embodiment is (Vs1_x, Vs1_y, Vs1_z) in the respective coordinate axes. Similarly, the interval between voxels (voxel size) of the second image is (Vs2_x, Vs2_y, Vs2_z) in the respective coordinate axes. For interpolation in this embodiment, for example, linear interpolation is used. In this processing step, the data obtaining unit 1010 outputs the above information regarding the voxel sizes of the first image and second image to the search area size obtaining unit 1040.

Note that in this embodiment, the intensity in the first image and the intensity in the second image are represented in the form of a function, as I1(x) and I2(x), respectively. Note that I1(x) and I2(x) are each a function that takes a corresponding three-dimensional position x in image coordinates as an argument and that returns the intensity in the corresponding image at the position. Regardless of positions of voxels that are present in a discretized manner in each image, this function takes, as arguments, given successive positions and returns the intensity through interpolation of voxels. The image processing apparatus 100 in this embodiment has the above interpolation processing function that is implemented when interpolation processing of image is performed in a sequence of processing described later.

In addition, although a case where linear interpolation is used as interpolation processing of image is described as an example in this embodiment, implementation of the present invention is not limited to this, and another interpolation method such as cubic interpolation or spline interpolation may also be used.

S2020: Obtain Deformation Information

In step S2020, the deformation information obtaining unit 1030 obtains deformation information such that voxels representing the same site substantially correspond to each other in the first image and the second image. That is, registration processing (deformation estimation processing) between the first image and the second image is performed. Then, the obtained deformation information is output to the position obtaining unit 1050.

In this embodiment, the deformation information is obtained by a known image processing technique. For example, the deformation information is obtained by deforming one of the images such that an image similarity level between the images after deformation is increased. As the image similarity level, a known method such as typically used sum of squared difference (SSD), mutual information amount, or mutual coefficient of correlation can be used. In addition, as an image deformation model, a deformation model based on a radial basis function such as thin plate spline (TPS) or a known deformation model such as free form deformation (FFD) or large deformation diffeomorphic metric mapping (LDDMM) can be used. Note that in a case where there are only differences in the position and posture between the first image and the second image (such approximation is feasible), rigid-body registration between the images may be performed to obtain transformation parameters of the position and posture as the deformation information. In addition, an affine transformation parameter between the images may be obtained as the deformation information. In a case where there is no false registration between the images (such approximation is feasible), the processing in this step is unnecessary.

The deformation information obtained through the above processing is represented as Def(x) in this embodiment. Note that Def(x) is a function that takes a three-dimensional position in image coordinates of the first image as an argument and that returns a three-dimensional position in image coordinates of the second image corresponding thereto.

S2030: Obtain Search Area Size

In step S2030, on the basis of the voxel size of the first image and the voxel size of the second image, the search area size obtaining unit 1040 obtains the search area size used for obtaining the difference value. Then, the obtained search area size is output to the search area setting unit 1060.

In this embodiment, the search area size is obtained on the basis of a characteristic related to the amount of a shift of discretization position at the time of image acquisition between the first image and the second image. Specifically, the characteristic that the position of a voxel at which an original image pickup signal of a subject is most reflected shifts between the first image and the second image by the sum of halves of voxel sizes of the respective images at most is used. This characteristic will be described later with reference to FIG. 11.

That is, the search area size obtaining unit 1040 obtains, as the search area size, the sum of halves of voxel sizes of both the first image and the second image. In this embodiment, the search area size is represented as Sx, Sy, Sz in the respective coordinate axes. That is, the search area size is obtained as $Sx=(Vs1\_x+Vs2\_x)/2$, $Sy=(Vs1\_y+Vs2\_y)/2$, and $Sz=(Vs1\_z+Vs2\_z)/2$.

Note that the search area size may be a value obtained by multiplying the above value (the sum of halves of voxel sizes of both the first image and the second image) by a predetermined coefficient. In addition, a predetermined search area size that is defined in advance may be set in accordance with the voxel sizes of the first image and the second image. Furthermore, a predetermined search area size that is defined in advance may also be used in accordance with the type of image (difference in modality or imaging method) or the type of site to be observed. Furthermore, a search area size that is set by a user in advance may also be used.

The processing from step S2040 to step S2060 described below is repeatedly executed until predetermined determination is made in determination processing in step S2070.

S2040: Obtain Positions

In step S2040, the position obtaining unit 1050 obtains the position of interest (voxel of interest) in the first image and obtains, by using the deformation information obtained in step S2020, the corresponding position in the second image corresponding to the position of interest. Then, the position obtaining unit 1050 outputs the obtained positions to the search area setting unit 1060 and the difference obtaining unit 1070. In this embodiment, the position of interest in the first image is denoted by pos1 and the corresponding position in the second image corresponding to the position of interest is denoted by pos2. In this processing step, specifically, calculation processing of pos2=Def(pos1) is performed.

S2050: Set Search Area

In step S2050, the search area setting unit 1060 sets the search area having the search area size (Sx, Sy, Sz) obtained in step S2030 in the neighborhood centered at the corresponding position pos2 in the second image. Then, the search area setting unit 1060 outputs information of the set search area to the difference obtaining unit 1070.

Figure 3:
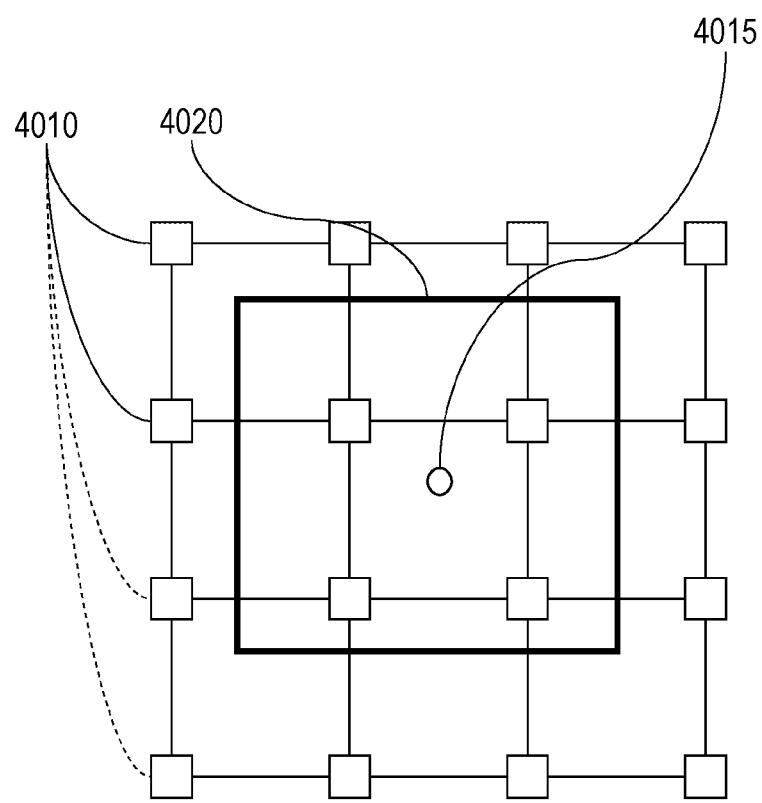
FIG. 3 is a diagram for describing an example of processing in step S2060 in the first embodiment.

This processing will be specifically described with reference to FIG. 3. Although the processing in this embodiment is performed on a three-dimensional image, a two-dimensional diagram is illustrated as an example in this description for the convenience of description on paper. In FIG. 3, reference numeral 4010 denotes voxels constituting the second image. The voxels 4010 herein are disposed to be arranged at equal intervals on every coordinate axis of the image coordinates of the second image. Reference numeral 4015 denotes the corresponding position pos2 obtained in step S2040. In addition, reference numeral 4020 denotes the search area that is set in this processing step. In this embodiment, the search area 4020 is a rectangular parallelepiped area centered at the corresponding position 4015. That is, a rectangular parallelepiped that has the position (pos2_x−Sx/2, pos2_y−Sy/2, pos2_z−Sz/2) and the position (pos2_x+Sx/2, pos2_y+Sy/2, pos2_z+Sz/2) as vertices on a diagonal and that is parallel to directions of coordinate axes is set as the search area. In this embodiment, this search area is also denoted by ω_pos2.

S2060: Obtain Difference Value

In step S2060, on the basis of the intensity at the position of interest post in the first image and the intensity in the second image in the search area ω_pos2 that is set in step S2030, the difference obtaining unit 1070 obtains the difference value to be given to the subtraction image. Then, the difference obtaining unit 1070 outputs the difference value to the subtraction image obtaining unit 1080. More specific processing is as follows. First, among intensities obtained by performing spatial and successive interpolation in the second image, which is a set of voxels arranged in a discretized manner, within the search area ω_pos2, an intensity I2_near that is the nearest to the intensity I1(pos1) at the position of interest pos1 in the first image is obtained. Then, a difference value I_diff=I1(pos1)−I2_near between I2_near and I1(pos1) is obtained.

FIG. 11 is diagrams for illustrating a process in which a difference is generated in a voxel value after discretization due to a shift of discretization position between images. FIG. 11A is graphs each illustrating a signal value on the vertical axis and a position in the x-axis direction on the horizontal axis. Although a graph 5000 and a graph 5040 are supposed to illustrate the same signal value, discretization positions are different. The discretization positions are illustrated by lines 5030 on the graphs.

FIG. 11B illustrates information of voxels generated by discretizing the graph 5000 and the graph 5040 in FIG. 11A and illustrates intensities on the vertical axis and positions in the x-axis direction on the horizontal axis. A voxel 5080 is a voxel generated from an area including a signal 5020 illustrated in FIG. 11A in a large amount and has a higher intensity than the other voxels in a graph 5070. Comparing the graph 5070 and a graph 5090 with each other, even voxels at the same position originating from the same signal have different voxel values due to a shift of discretization position.

FIG. 11C is graphs illustrating intensities and positions of voxels obtained through resolution conversion of the voxels illustrated in the graph 5070 and the graph 5090 in FIG. 11B. The resolution conversion is processing in which, for example, voxels are upsampled and the intensity is interpolated by nearest neighbor interpolation, linear interpolation, cubic interpolation, or the like. In FIG. 11C, a voxel 5110 is a voxel where the signal 5020 is most reflected, and a voxel 5130 is a voxel where a signal 5060 is most reflected.

As illustrated in FIGS. 11A to C, even with the voxel value originating from the same signal, due to a shift of discretization position, as illustrated in FIG. 11B and FIG. 11C, a shift is generated between the positions of voxels where the signal is most reflected. Due to a shift of discretization position of a signal, the voxel where the signal is most reflected is assumed to shift by half a voxel at most from the position of the original signal.

In subtraction processing between images that are considered to be obtained by converting the same signal, the difference between voxel values is preferably zero. However, as described above, the difference between voxel values at the same position is not always zero due to a shift of discretization position. Accordingly, in this embodiment, I2_near is obtained. In a case where the voxel 5080 in FIG. 11B is set as the position of interest pos1, an object of this embodiment is, for example, to search for and obtain the intensity at the voxel 5130 as I2_near.

Note that as a simple method for obtaining I2_near, it is considered that interpolation processing is successively performed on the second image in a range of the search area ω_pos2 and the interpolation results and I1(pos1) are compared with each other. However, a truly successive interpolation processing requires an infinite number of times of interpolation processing and comparison processing. Thus, typically in a well-known method, the search area ω_pos2 is sampled with an appropriate step size, and a finite number of times of processing is performed at the sampling positions to obtain an approximate solution.

This embodiment will describe, instead of the above method for obtaining an approximate solution, a method of a finite number of times of calculation processing to obtain a solution that is theoretically obtained by successive interpolation processing.

Figure 4:
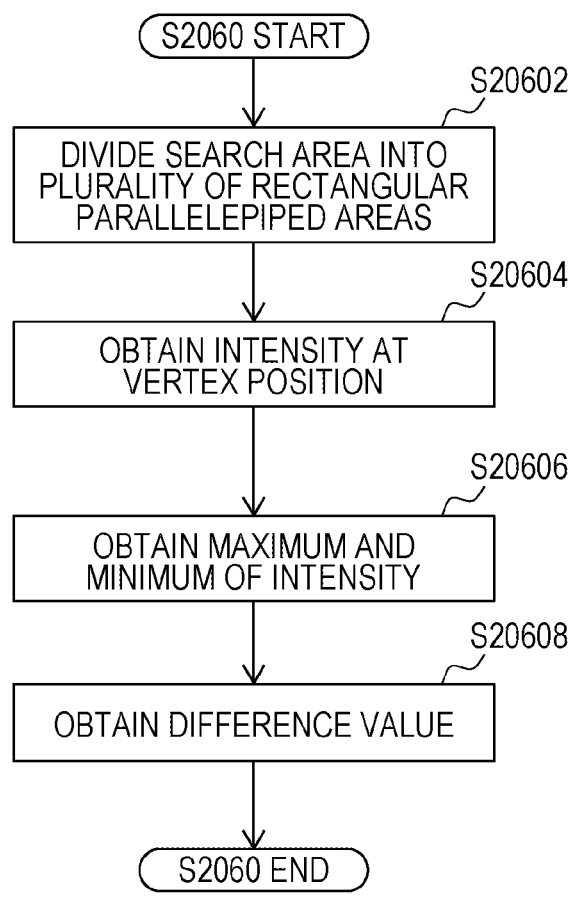
FIG. 4 is a flowchart for describing an example of processing in step S2060 in the first embodiment.

The processing in step S2060 by this method will be specifically described with reference to the flowchart in FIG. 4.

S20602: Divide Search Area into Plurality of Rectangular Parallelepiped Areas In step S20602, the difference obtaining unit 1070 performs processing on the search area ω_pos2 that is set in the processing in step S2050 for dividing the area into a plurality of rectangular parallelepiped areas. Note that each of the plurality of rectangular parallelepiped areas obtained by dividing the search area is an example of a partial area included in the search area. The rectangular parallelepiped areas are parallel to image coordinate axes of the second image.

Figure 5:
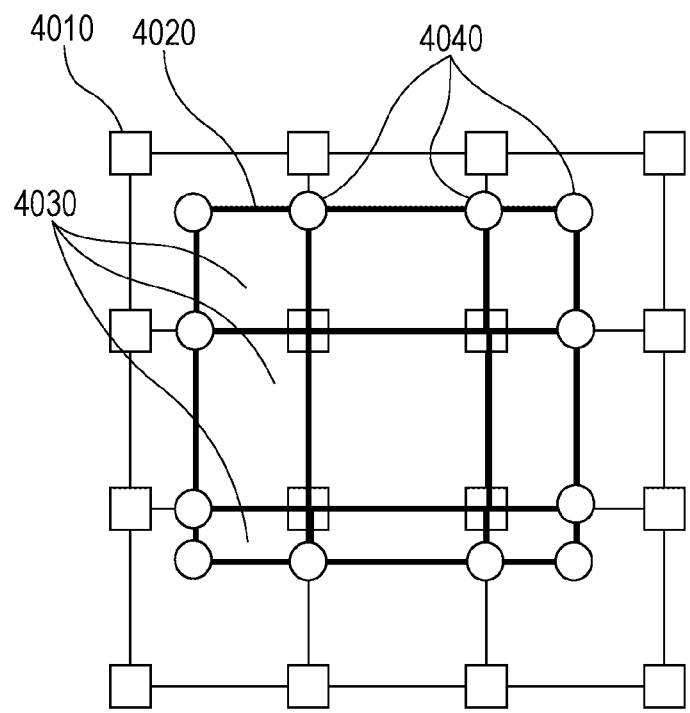
FIG. 5 is a diagram for describing an example of processing in step S20602 in the first embodiment.

This processing will be specifically described with reference to FIG. 5. Although the processing in this embodiment is performed on a three-dimensional image, a diagram of a two-dimensional case is illustrated as an example in this description for the convenience of description on paper. In FIG. 5, reference numeral 4010 denotes the voxels constituting the second image, and reference numeral 4020 denotes the search area ω_pos2 that is set through the processing in step S2050. Reference numeral 4030 denotes the rectangular parallelepiped areas obtained by dividing the search area 4020. In this processing step, processing for dividing the search area 4020 into the rectangular parallelepiped areas 4030 by a method described below is performed. First, intersection points between the outline of the search area 4020 and lines connecting adjacent voxels among the voxels 4010 are set as division vertices 4040. In addition, the vertex positions of the search area 4020 are similarly set as the division vertices 4040. Furthermore, among the voxels 4010, positions of voxels included in the search area 4020 are also set as the division vertices 4040. Then, the search area 4020 is divided into rectangular parallelepiped areas having the division vertices 4040 that are set through the above processing to obtain the rectangular parallelepiped areas 4030. In this embodiment, a case where the search area 4020 is divided into N_sr rectangular parallelepiped areas 4030 will be described as an example. Positions of the vertices 4040 of the divided rectangular parallelepiped areas 4030 are denoted by V_ij in this embodiment. Note that a subscript i represents an index of the N_sr rectangular parallelepipeds. In addition, j represents an index of each of the eight vertices of a rectangular parallelepiped. That is, $1 \le i \le N\_sr$ and $1 \le j \le 8$ are satisfied.

S20604: Acquire intensity at Vertex Position

In step S20604, the difference obtaining unit 1070 performs processing for obtaining an intensity I2_s_ij in the second image at each of the vertex positions V_ij of the N_sr rectangular parallelepiped areas 4030 obtained by the dividing in step S20602. That is, calculation processing of I2_s_ij=I2(V_ij) is performed. Note that if a position V_ij is identical with the position of any of the voxels 4010, the voxel value is obtained as I2_s_ij; if not, the intensity in the second image at the position V_ij is obtained through interpolation processing.

S20606: Acquire Maximum and Minimum of Intensity

In step S20606, the difference obtaining unit 1070 performs processing for obtaining a maximum I2_max and a minimum I2_min of the intensity I2_s_ij ($1 \le i \le N\_sr$, $1 \le j \le 8$) at all the vertex positions obtained in step S20604.

$$\text{I2\_max} = \max_{1 \le i \le N\_sr, 1 \le j \le 8} \{\text{I2\_s\_ij}\}$$

$$\text{I2\_min} = \min_{1 \le i \le N\_sr, 1 \le j \le 8} \{\text{I2\_s\_ij}\}$$

I2_max obtained as above denotes the maximum intensity within the search area ω_pos2, and I2_min denotes the minimum intensity within the search area ω_pos2. In this light, the difference obtaining unit 1070 is an example of second obtaining means that obtains a maximum or a minimum of a voxel value or an interpolated value within a search area on the basis of at least one of a voxel value included in a partial area included in the search area and an interpolated value obtained by interpolation of a voxel of the second image, which is the target image.

Note that a vertex position V_ij of a rectangular parallelepiped area 4030 may be identical with a voxel of the second image. In this case, the intensity I2_s_ij is the voxel value of the voxel. Thus, the intensity I2_s_ij is at least one of a voxel value and an interpolated value within the search area.

S20608: Acquire Difference Value

In step S20608, the difference obtaining unit 1070 performs processing for obtaining the difference value I_diff on the basis of the intensity I1(pos1) at the position of interest pos1 in the first image obtained in step S2040 and the maximum I2_max and minimum I2_min obtained in S20606. Specifically, the difference value I_diff is obtained by calculation illustrated in Math 2.

$$I\_diff = \begin{cases} 0: & \text{where } I2\_min \leq I1(pos1) \leq I2\_max \\ I1(pos1) - I2\_min: & \text{where } I1 < I2\_min \\ I1(pos1) - I2\_max: & I1 > I2\_max \end{cases}$$

That is, in a case where the intensity I1(pos1) is included in the range from the minimum I2_min to the maximum I2_max, 0 is set as the difference value I_diff. On the other hand, in a case where the intensity I1(pos1) is less than the minimum I2_min, a difference between the intensity I1(pos1) and the minimum I2_min is set as the difference value I_diff. In addition, in a case where the intensity I1(pos1) is greater than the maximum I2_max, a difference between the intensity I1(pos1) and the maximum I2_max is set as the difference value I_diff. Thus, as the difference value I_diff, a value having the smallest absolute value is set among possible values as difference values between I1(pos1) and I2 at various positions within the search area.

Through the above processing from step S20602 to S20608, the processing in step S2060 in this embodiment is performed.

The above processing corresponds to processing for obtaining a maximum and a minimum of the intensity in a case where linear interpolation processing is performed on the second image within the search area 4020 and for obtaining a difference value by comparing the maximum and minimum with an intensity at a position of interest in the first image. This can be confirmed as follows. That is, (1) an intensity in an interpolated image obtained by linear interpolation of image with a predetermined rectangular parallelepiped area does not exceed the range between the maximum and the minimum of the intensity at the vertex positions of the rectangular parallelepiped. In addition, (2) in an image obtained by successive linear interpolation within a predetermined area, any intensity between the maximum and the minimum of the interpolated value exists within the area. Thus, the maximum and the minimum of the intensity in a case where linear interpolation is performed in the rectangular parallelepiped area correspond with the maximum and the minimum of the intensity at the vertex positions of the rectangular parallelepiped. In addition, the maximum and the minimum of the intensity in a case where linear interpolation is performed in a given area constituted by combining a plurality of rectangular parallelepipeds correspond with the maximum and the minimum of the intensity at the vertex positions of each of the rectangular parallelepipeds constituting the area.

Although a case where linear interpolation is used as a method for interpolation processing of image has been described in the above example, any interpolation processing may be performed as long as the range between the maximum and the minimum of the intensity at the vertex positions are not exceeded by the interpolation processing. Even with interpolation processing by which the range between the maximum and the minimum of the intensity at the vertex positions may be exceeded, use of the maximum and the minimum of the intensity at the vertex positions as approximates of the maximum and the minimum of the intensity in an interpolated area is also an embodiment of the present invention.

According to the above processing, in a case where successive interpolation is performed in the second image, the difference value between the intensity within the range of the search area 4020 and the intensity at the position of interest in the first image can be efficiently obtained.

S2070: Change Position of interest

In step S2070, the position obtaining unit 1050 determines whether the difference value has been obtained at positions in the first image. If the difference value at all positions has been obtained, the processing proceeds to step S2080. On the other hand, if the difference value at all positions has not been obtained, the processing returns to step S2040. Then, a position (voxel) at which the difference value is yet to be obtained in the first image is set as a new position of interest (voxel of interest), and the processing in and after step S2040 is performed again.

Note that in this embodiment, the difference value may be obtained not at all positions (all voxels) in the first image, but at some positions in the first image that are extracted in advance by a known image processing technique, for example, only voxels representing an area of an organ of interest. In addition, positions of interest may be voxels that are thinned out at a predetermined interval. This can reduce a processing time required for reducing noise.

S2080: Obtain Subtraction Image

In step S2080, the subtraction image obtaining unit 1080 obtains a subtraction image in which the intensity is the difference value at each position (voxel of interest) in the first image. Then, the subtraction image obtaining unit 1080 stores the obtained subtraction image in the data server 110. In addition, the subtraction image obtaining unit 1080 outputs the subtraction image to the display control unit 1090.

S2090: Display Subtraction Image

In step S2090, the display control unit 1090 performs control to cause the display unit 120 to display the subtraction image (first subtraction image) obtained in step S2080.

As a display example, for example, a tomography image or a projection image of each image (three-dimensional image) may be displayed. For example, a screen may be longitudinally or laterally divided to arrange the first image, the second image, and the subtraction image for display. In addition, a subtraction image drawn in different color from the first image or the second image may be superposed for display, or only one of the first image, the second image, and the subtraction image may be selected (may be freely switched at the same position) for display. Furthermore, in accordance with a resolution of any of the images, other images may be enlarged or reduced for display, or the respective images may be arranged for display such that the corresponding position in the second image corresponding to the single position of interest in the first image matches the position of interest in the subtraction image.

Thus, the processing of the image processing apparatus 100 is performed.

From the above, the difference value obtained by searching an area of an appropriate size considering a shift of discretization position can be obtained with a high calculation efficiency. This makes it possible to provide a user with a subtraction image in which necessary signals in the subtraction image remain and noise generated from a difference in intensity due to a shift of discretization position between images is reduced.

Modification 1-1

Case where Search Area is Ellipsoid

The first embodiment of the present invention has described as an example a case where the shape of the search area that is set in step S2050 is a rectangular parallelepiped. However, the implementation of the present invention is not limited to this, and a given shape may be employed. For example, the search area may be an ellipsoid area having a size determined on the basis of the search area size obtained in step S2030. This case will be described with reference to FIG. 6.

Figure 6A:
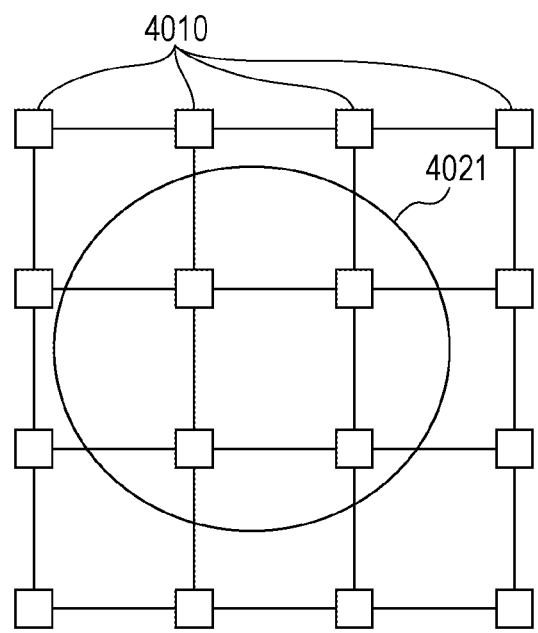
FIG. 6A is a diagram for describing an example of a modification in the first embodiment.
Figure 6B:
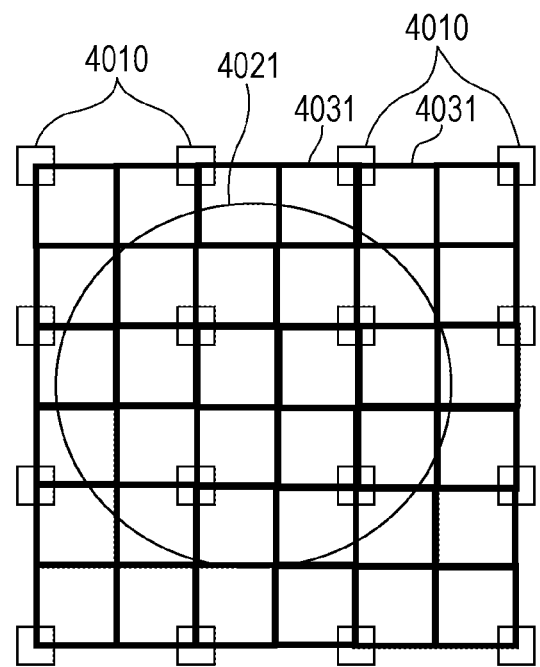
FIG. 6B is a diagram for describing an example of a modification in the first embodiment.
Figure 6C:
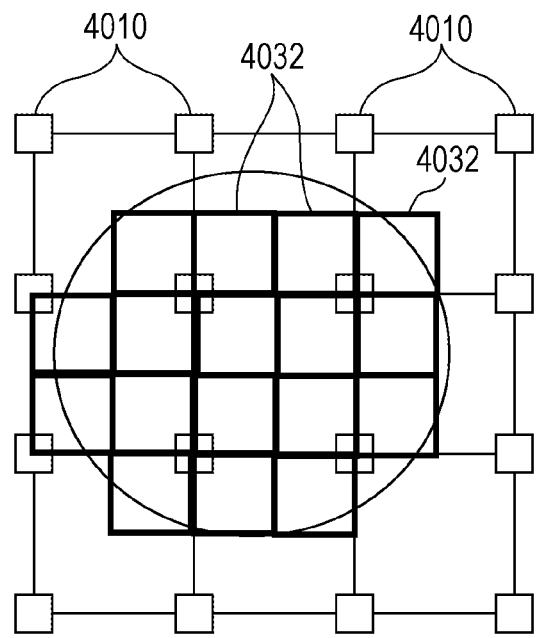
FIG. 6C is a diagram for describing an example of a modification in the first embodiment.
Figure 6D:
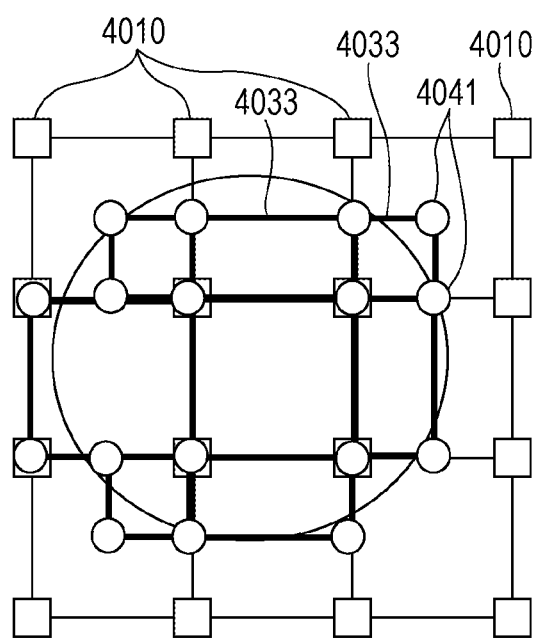
FIG. 6D is a diagram for describing an example of a modification in the first embodiment.

In FIG. 6A, reference numeral 4010 denotes the voxels constituting the second image. Reference numeral 4021 denotes an ellipsoid search area that is set in step S2050 on the basis of the search area size obtained in step S2030. As an example of the shape of the search area 4021, diameters of the ellipsoid in the axis directions can be set on the basis of the size Sx, Sy, Sz in the axis directions obtained in step S2030. For example, constant multiples of Sx, Sy, Sz are set as the diameters of the ellipsoid in the axis directions. Then, as the processing in step S20602, as illustrated in FIG. 6B, processing for obtaining a plurality of subdivided rectangular parallelepipeds 4031 to include the above search area is performed. Each of the rectangular parallelepipeds has in each axis direction a size of half the voxel interval between the voxels 4010. From among the subdivided rectangular parallelepipeds, rectangular parallelepipeds of which greater than or equal to half the volume overlaps with the search area 4021 are selected, and thereby selected rectangular parallelepipeds 4032 illustrated in FIG. 6C are obtained. Then, in the selected rectangular parallelepipeds 4032, adjacent ones are coupled as illustrated in FIG. 6D to be transformed into a rectangular parallelepiped set 4033 constituted by a smaller number of vertices. Then, the processing in and after step S20604 is performed on the rectangular parallelepiped set 4033. Note that although a case where rectangular parallelepipeds are generated by dividing each interval between voxels into two parts have been described as an example in FIG. 6, the number of parts obtained by the dividing may be other numbers (for example, three parts may be generated by the dividing, or the dividing may not be performed).

Through the above processing, it is possible to set, as the search area, a shape other than the rectangular parallelepiped search area described in the first embodiment. Thus, an appropriate search area in accordance with imaging characteristics (e.g., discretization characteristics) of a modality that picks up the first image and the second image can be set. This produces an effect of obtaining a subtraction image with a higher quality.

Second Embodiment

The first embodiment has described as an example a case of obtaining intensities at all the vertex positions of the rectangular parallelepipeds, obtained by the dividing in step S20602, and the maximum and the minimum thereof. However, the implementation of the present invention is not limited to this. A second embodiment of the present invention will describe a processing procedure for obtaining the maximum and the minimum more efficiently.

The functional configuration of an image processing apparatus according to the second embodiment is substantially the same as the functional configuration of the image processing apparatus according to the first embodiment, and thus, FIG. 1 is used as a diagram for describing the functional configuration of the image processing apparatus according to this embodiment. A detailed description is omitted herein.

Figure 7:
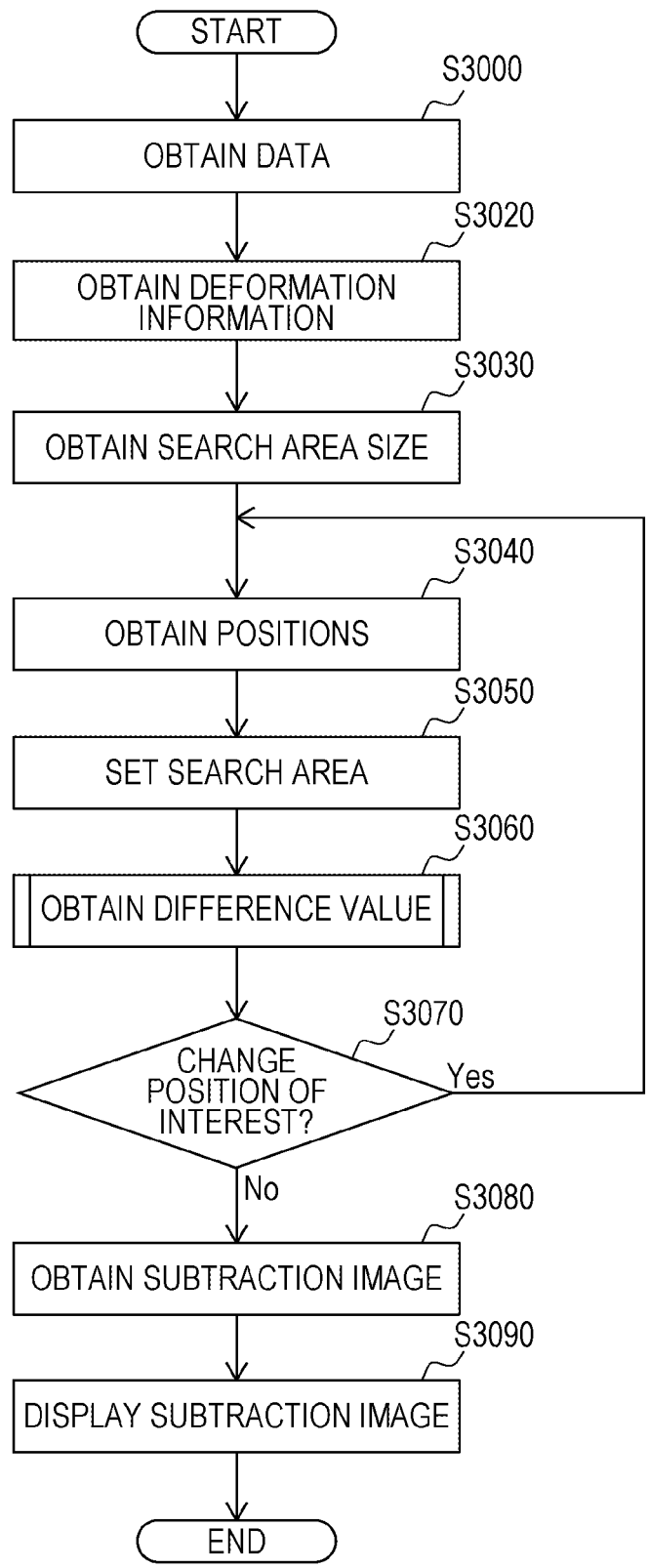
FIG. 7 is a flowchart illustrating an example of an entire processing procedure in a second embodiment.

FIG. 7 illustrates an entire processing flow executed by the image processing apparatus according to the second embodiment. The processing from step S3000 to step S3050 in the second embodiment is substantially the same as the processing from step S2000 to step S2050 in the first embodiment, and thus, description is omitted herein. In addition, the processing from step S3070 to step S3090 is substantially the same as the processing from step S2070 to step S2090 in the first embodiment, and thus, description is omitted herein.

Now, step S3060 of which the processing content is different from that in the first embodiment will be described.

S3060: Obtain Difference Value

Figure 8:
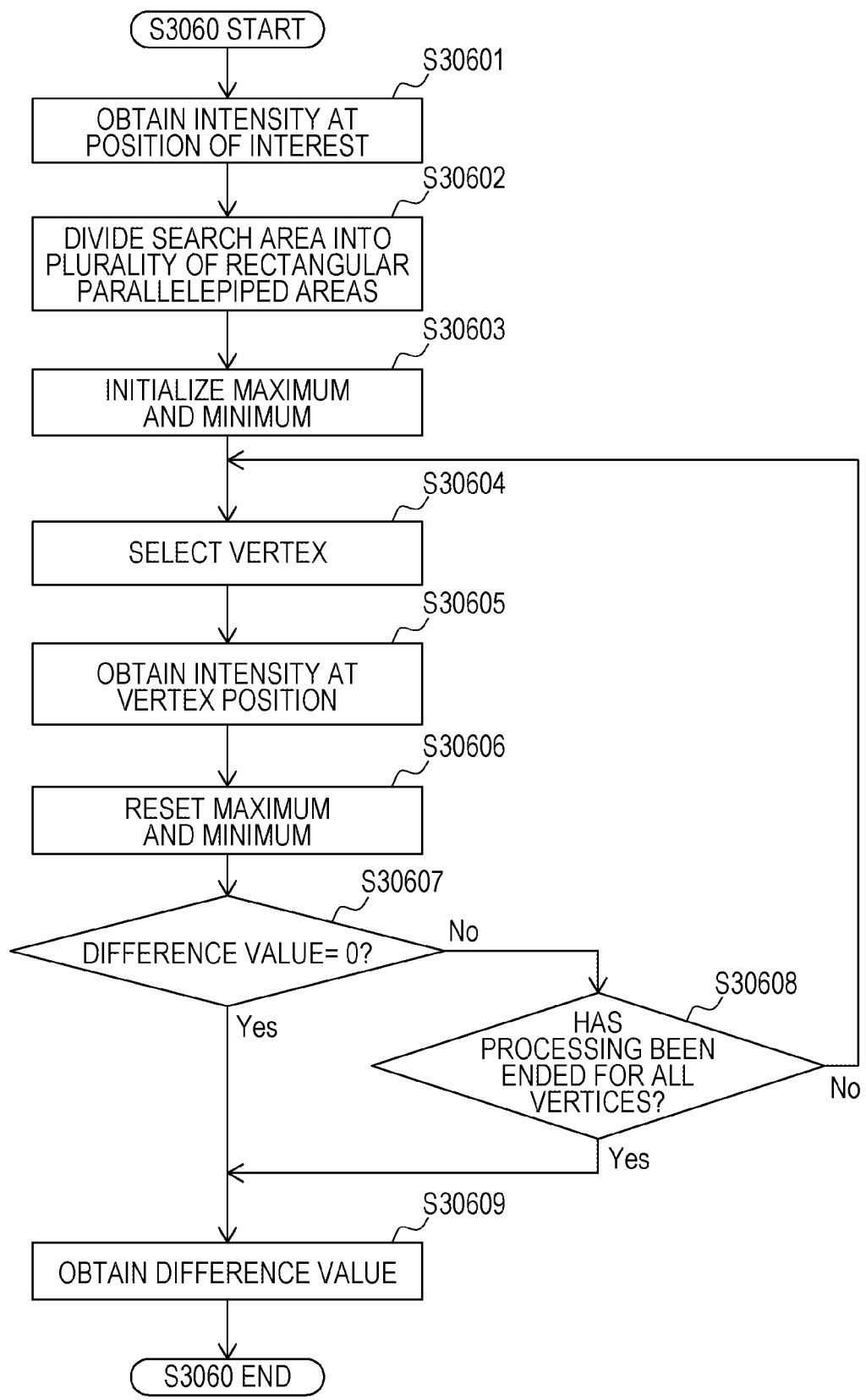
FIG. 8 is a flowchart for describing an example of processing in step S3060 in the second embodiment.

In step S3060, on the basis of the intensity at the position of interest pos1 in the first image and the intensity in the second image in the search area ω_pos2 that is set in step S3030, the difference obtaining unit 1070 obtains the difference value to be given to the subtraction image. Then, the difference obtaining unit 1070 outputs the obtained difference value to the subtraction image obtaining unit 1080. FIG. 8 is a flowchart for specifically describing the processing in step S3060 performed by the image processing apparatus in the second embodiment. The following description is given in accordance with the flowchart.

S30601: Obtain Intensity at Position of Interest

In step S30601, the difference obtaining unit 1070 performs processing for obtaining an intensity I1_s at the position of interest in the first image.

S30602: Divide Search Area into Plurality of Rectangular Parallelepiped Areas

In step S30602, the difference obtaining unit 1070 performs processing for dividing the search area that is set in step S3050 into a plurality of rectangular parallelepipeds. This processing is substantially the same as the processing in step S20602 in the first embodiment, and thus, a detailed description is omitted.

S30603: Initialize Maximum and Minimum

In step S30603, the difference obtaining unit 1070 initializes scalar variables I_max and I_min to the value 0, which are to be reset through repetitive processing from step S30604 to step S30608, which will be described later.

Subsequently, while sequentially switching the vertex position as a processing target among the respective vertex positions V_ij of a divided rectangular parallelepiped obtained in step S30602, the processing from step S30604 to step S30608 is repetitively performed. During the repetitive processing, the variables I_max and I_min are reset as appropriate.

S30604: Select Vertex

In step S30604, from among the plurality of vertex positions V_ij as processing targets, the difference obtaining unit 1070 selects a vertex for which the processing in and after step S30605, which will be described later, is yet to be performed, and the processing proceeds to the following step.

In this example, as an example, the processing from step S30604 to step S30608 is repetitively performed in a double loop while changing each of i and j, which are subscripts of V_ij, in ascending order. Then, a case will be described where it is determined in step S30608 whether the processing at all the vertices has ended. In the following description, the vertex position selected in step S30604 is V_sel.

S30605: Acquire intensity at Vertex of Divided Rectangular Parallelepiped

In step S30605, the difference obtaining unit 1070 performs processing for obtaining an intensity I2_sel=I2(V_sel) in the second image at the vertex position V_sel selected in step S30604. This processing is performed as substantially the same processing as that in step S20604 in the first embodiment, and thus, a detailed description is omitted herein.

S30606: Reset I_max, I_min

In step S30606, the difference obtaining unit 1070 performs processing for resetting the variables I_max and I_min on the basis of the intensity I2_sel obtained in step S30604. Specifically, if the variable I_max before execution of this processing step is less than I2_sel, the difference obtaining unit 1070 resets I_max to I2_sel. In addition, if the variable I_min is greater than I2_sel, the difference obtaining unit 1070 resets I_min to I2_sel. Note that if this processing step is initially performed, regardless of the values of the variables I_max and I_min before execution of this processing step, the respective variables are reset to I2_sel.

S30607: Compare intensity I1_s with I_max, I_min

In step S30607, the difference obtaining unit 1070 determines whether the intensity I1_s at the position of interest in the first image obtained in step S30601 and the values of the variables I_max and I_min reset in step S30606 satisfy a predetermined condition. The predetermined condition is, for example, a magnitude relationship among the intensity I1_s, the maximum I_max, and the minimum min. Specifically, if I_min≤I1_s≤I_max is satisfied, the reset processing of the maximum and the minimum is stopped, and the processing proceeds to step S30609. On the other hand, if not, the processing proceeds to step S30608.

S30608: Change Vertex for which Processing is Performed

In step S30608, the difference obtaining unit 1070 determines whether processing has been performed for all the vertex positions V_ij of the divided rectangular parallelepipeds obtained in step S30602. If processing has been performed for all the vertex positions V_ij, the processing proceeds to step S30609. If not, the processing proceeds to step S30604 to continue the processing related to the vertex positions for which processing is yet to be performed.

S30609: Acquire Difference Value

In step S30609, the difference obtaining unit 1070 obtains the difference value I_diff on the basis of I1_s obtained in step S30601 and I_max and I_min reset through the repetitive processing from step S30604 to step S30608. Specifically, I_diff is obtained by calculation processing illustrated in Math 3.

$$\text{I\_diff} = \begin{cases} 0: & \text{where I\_min} \leq \text{I1\_s} \leq \text{I\_max} \\ \text{I1\_s} - \text{I\_min}: & \text{where I1\_s} < \text{I\_min} \\ \text{I1\_s} - \text{I\_max}: & \text{I1\_s} > \text{I\_max} \end{cases}$$

Through the above-described processing from step S30601 to S30609, the processing in step S3060 in this embodiment is performed.

Through the above-described procedure, the processing of the image processing apparatus according to the second embodiment is performed. Since the second embodiment has an effect of reducing the number of times of image interpolation processing at vertex positions compared with the first embodiment, an effect of performing processing with a higher calculation efficiency is produced.

Modification 2-1

Calculate Interpolation-Unnecessary End Point First

During the processing in step S3060 in the above second embodiment, a case where processing is sequentially performed while changing each of i and j, which are subscripts of the vertex positions V_ij of the rectangular parallelepipeds obtained by the dividing in step S30602, in ascending order has been described as an example. However, the implementation of the present invention is not limited to this. For example, the difference obtaining unit 1070 defines the order of processing on the basis of a level of calculation cost for obtaining the voxel value or interpolated value at a vertex position. Specifically, in step S30604, the difference obtaining unit 1070 may preferentially select from V_ij a vertex at the position identical with the position of a voxel of the second image (vertex position at which the voxel value is directly available as the intensity without interpolation). Thus, as the processing in step S30605, processing is performed first for a vertex for which interpolation processing is unnecessary and the calculation cost is low. Depending on the condition determination in step S30607, the repetitive processing from step S30604 to step S30608 may be stopped without performing operation for all the vertices. Accordingly, by changing the processing order by the above method, further increase in calculation efficiency is expected compared to the second embodiment.

Modification 2-2

Reset Only Either Maximum or Minimum

During the processing in step S3060 in the above second embodiment, a case where the processing from step S30604 to step S30606 is repetitively performed so as to obtain the maximum and the minimum of the intensity in the second image within the search area has been described as an example. However, the implementation of the present invention is not limited to this. For example, when the repetitive processing from step S30604 to step S30606 is initially performed, it is determined whether the intensity at the vertex position as a processing target obtained in step S30605 is greater than or less than the intensity at the position of interest in the first image. For example, if the intensity I2_sel at the vertex position as a processing target is greater than the intensity I1_s at the position of interest, in the second time and subsequent times of the above repetitive processing, the minimum I_min of the intensity at the vertex position as a processing target is reset, and reset of the maximum I_max can be skipped. Then, in step S30607, if the above minimum I_min is less than the intensity I1_s at the position of interest, the difference value I_diff is set to 0, and the processing proceeds to step S30609. If not, calculation I_diff=I1_s−I_min is performed, and the processing proceeds to step S0608. Similarly, if I2_sel is less than s when the repetitive processing is initially performed, in the second time and subsequent times of the above repetitive processing, the maximum I_max of the intensity at the vertex position as a processing target is reset, and reset of the minimum I_min can be skipped. Then, in step S30607, if the above maximum I_max is greater than the intensity I1_s at the position of interest, the difference value I_diff is set to 0, and the processing proceeds to step S30609. If not, calculation I_diff=I1_s−I_max is performed, and the processing proceeds to step S30608.

According to the above method, the repetitive processing from step S30604 to step S30606 can be simplified to processing for resetting only either the maximum or the minimum. Accordingly, increase in calculation efficiency is expected. In this light, the difference obtaining unit 1070 is an example of second obtaining means for obtaining, in a partial area included in the search area, on the basis of at least one of a voxel value included in the partial area and an interpolated value obtained by interpolation of a voxel of the second image, which is the target image, at least one of a maximum and a minimum of a voxel value and an interpolated value within the search area.

Modification 2-3

Select End Point for which Interpolated Value is to be Calculated (Skip Processing for Calculation-Unnecessary End Point)

During the processing in step S3060 in the above second embodiment, a case where the vertex positions V_ij for which processing is yet to be performed are sequentially selected without conditions as the vertex position as a processing target in step S30604 to perform the processing from step S30605 to S30607 has been described as an example. However, the implementation of the present invention is not limited to this. For example, instead of selecting the vertex positions V_ij for which processing is yet to be performed without conditions, the following condition determination may be made in step S30604, and depending on the result, it may be selected whether to perform the processing from step S30605 to step S30607. A processing method in this case will be described with reference to FIG. 9.

Figure 9:
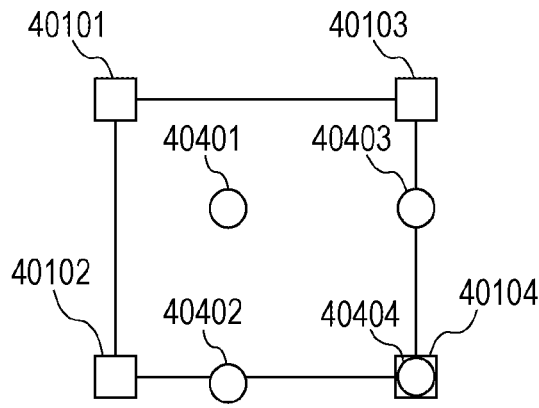
FIG. 9 is a diagram for describing an example of a modification in the second embodiment.

In FIG. 9, reference numerals 40101 to 40104 denote voxels of the second image. In addition, reference numerals 40401 to 40404 denote vertex positions of a rectangular parallelepiped obtained by the dividing in step S30602. In a case where the vertex position 40401 is focused, in step S30605 in the second embodiment, the intensity at this position in the second image is obtained by interpolation of a voxel value from the voxels 40101 to 40104. Then, in step S30606, on the basis of the interpolated value, I_min and I_max are reset. However, in a case where each voxel value of the voxels 40101 to 40104 used for obtaining the interpolated value falls within the range from I_min to I_max, the processing from step S30605 to step S30607 for this vertex may be skipped. That is, by assuming that processing for this vertex position has already been performed, the processing may proceed to step S30608 without performing the processing from step S30605 to S30607. Even if the processing is performed in this manner, the difference value obtained in step S3060 is equal to the difference value obtained if the processing is performed as in the second embodiment. This is attributed to a characteristic that the intensity at the vertex position obtained by interpolation of the voxels 40101 to 40104 does not exceed the maximum or fall below the minimum of the voxel values of voxels used for interpolation processing. In other words, in a case where each voxel value of the voxels 40101 to 40104 falls within the range from I_min to I_max, it is obvious that the intensity at the vertex 40401 in the second image also falls within the range from I_min to I_max. That is, even if the intensity at this vertex position is obtained by interpolation processing in step S30605, I_min and I_max are not reset in the subsequent step S30606. Therefore, skipping the processing from step S30605 to step S30607 does not influence the result.

In addition, in a case where the vertex 40402 is a processing target in FIG. 9, it is determined whether voxel values of the voxels 40102 to 40104 used for obtaining the intensity at this position by interpolation fall within the range from I_min to I_max. Then, determination as to whether to skip the processing may be made as in the above case.

According to the above-described method, the number of times of interpolation processing of the intensity in the second image can be reduced without changing the calculation results. Accordingly, further increase in calculation efficiency is expected compared to the second embodiment.

Modifications

The above embodiments have described a case where the data obtaining unit 1010 obtains the first image and the second image from the data server 110 as an example. However, the implementation of the present invention is not limited to this. For example, the data obtaining unit 1010 may obtain at least one of the first image and the second image from a modality (not illustrated).

The present invention can be implemented by a process in which a program for implementing one or more functions in the above embodiments is supplied to a system or an apparatus via a network or a storage medium and one or more processors in a computer of the system or apparatus reads and executes the program. The present invention can also be implemented by a circuit (e.g., ASIC) for implementing one or more functions.

The image processing apparatus in each of the above embodiments may be realized as a standalone apparatus, or the above-described processing may be performed by combining a plurality of apparatuses so that mutual communication is possible. Either form is included in the embodiments of the present invention. The above-described processing may also be performed by a shared server apparatus or server group. The image processing apparatus and a plurality of apparatuses that constitute an image processing system are at least capable of performing communication at a predetermined communication rate and are not necessarily present in the same facility or the same country.

The embodiments of the present invention include a form in which a software program for implementing the functions in the above embodiments is supplied to a system or an apparatus and a computer of the system or apparatus reads and executes the code of the supplied program.

Therefore, the program code itself to be installed in the computer in order to perform the processing according to the embodiments with the computer is another embodiment of the present invention. In addition, on the basis of an instruction included in the program read by the computer, an OS or the like running on the computer may perform part or all of the actual processing, and the processing may implement the functions in the above embodiments.

A form in which the above embodiments are combined as appropriate is also included in the embodiments of the present invention.

The present invention is not limited to the above embodiments, and various modifications and alterations can be made without departing from the spirit and scope of the present invention. Therefore, the claims are attached as follows to make public the scope of the present invention.

According to the image processing apparatus according to the embodiment of present invention, it is possible to perform more efficient calculation for obtaining the voxel having the closest luminance from the neighborhood of the corresponding voxel.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a memory storing a program; and
one or more processors which, by executing the program, function as:
first obtaining means for obtaining a target image constituted by a set of voxels arranged in a discretized manner, wherein each point of the set of voxels constituting the target image is represented with one coordinate;
setting means for setting a search area in the target image, wherein at least one of vertexes of the search area is different from points of the voxels of the target image;
dividing means for dividing the search area into a plurality of partial areas on the basis of positions of points of the voxels of the target image, wherein at least some of the partial areas include at least one of the points of the voxels of the target image as a respective vertex, and wherein at least some of the partial areas respectively include at least one vertex that is not one of the points of the voxels;
interpolating means for generating an interpolated value, wherein generating the interpolated value includes interpolating a voxel value of the target image at a position of a vertex of the vertexes of the plurality of partial areas, wherein the vertex is not any of the points of the voxels; and
second obtaining means for obtaining, on the basis of the interpolated value and a voxel value of a voxel having one of the points that is one of the vertexes of at least one of the plurality of partial areas, at least one of (i) a maximum of a voxel value and an interpolated value within the search area and (ii) a minimum of a voxel value and an interpolated value within the search area.

2. The image processing apparatus according to claim 1, wherein the first obtaining means further obtains a reference image, and
wherein the setting means sets the search area on the basis of position in the target image corresponding to a position of interest in the reference image.

3. The image processing apparatus according to claim 2, further comprising third obtaining means for obtaining a comparison value through a comparison operation between at least one of the maximum and the minimum obtained by the second obtaining means and a voxel value at the position of interest in the reference image.

4. The image processing apparatus according to claim 3, wherein, in the comparison operation between the voxel value at the position of interest and at least one of the maximum and the minimum, the third obtaining means obtains, as the comparison value, a value having a smallest absolute value among possible values as difference values between the voxel value and the interpolated value within the search area and the voxel value at the position of interest.

5. The image processing apparatus according to claim 3, wherein the third obtaining means (1) sets the comparison value to 0 if the voxel value at the position of interest is less than or equal to the maximum and greater than or equal to the minimum, (2) sets the comparison value to a difference value between the voxel value and the maximum if the voxel value at the position of interest is greater than the maximum, and (3) sets the comparison value to a difference value between the voxel value and the minimum if the voxel value at the position of interest is less than the minimum.

6. The image processing apparatus according to claim 3, wherein the third obtaining means performs repetitive processing for obtaining the maximum and the minimum while sequentially switching a vertex as a processing target among vertices of each partial area included in the search area and, if a magnitude relationship among the voxel value at the position of interest in the reference image, the maximum, and the minimum satisfies a predetermined condition, ends the repetitive processing.

7. The image processing apparatus according to claim 6, wherein the predetermined condition is that the voxel value at the position of interest is less than or equal to the maximum and greater than or equal to the minimum.

8. The image processing apparatus according to claim 6, wherein, in the repetitive processing, on the basis of a level of calculation cost for obtaining the voxel value and interpolated value of the target image at the vertex position, the third obtaining means defines an order of processing.

9. The image processing apparatus according to claim 3, wherein, on the basis of the position of interest in the reference image and information regarding deformation for registration between the target image and the reference image, the third obtaining means obtains information regarding the corresponding position.

10. The image processing apparatus according to claim 3, further comprising fourth obtaining means for obtaining a subtraction image on the basis of the comparison value obtained by the third obtaining means.

11. The image processing apparatus according to claim 3, further comprising display control means for causing a display unit to display a subtraction image obtained on the basis of the comparison value obtained by the third obtaining means.

12. The image processing apparatus according to claim 1, wherein the search area is a rectangular parallelepiped area parallel to image coordinate axes of the target image.

13. The image processing apparatus according to claim 1, wherein the second obtaining means obtains at least one of a maximum value or a minimum value that is possible as an interpolated value of a pixel at an arbitrary position in the search area.

14. An image processing apparatus comprising:
a memory storing a program; and
one or more processors which, by executing the program, function as:
first obtaining means configured to obtain a target image constituted by a set of voxels arranged in a discretized manner and a reference voxel;
setting means configured to set a search area in the target image on the basis of a correspondence position that is a position in the target image corresponding to a position of interest in the reference image;
interpolating means for generating an interpolated value, wherein generating the interpolated value includes interpolating a voxel value in a partial area included in the search area;
second obtaining means configured to obtain on the basis of a voxel value included in the partial area and the interpolated value, at least one of (i) a maximum of a voxel value and an interpolated value within the search area and (ii) a minimum of a voxel value and an interpolated value within the search area; and third obtaining means configured to obtain a comparison value through a comparison operation between a voxel value at the position of interest in the reference image and at least one of the maximum and the minimum obtained by the second obtaining means, wherein the third obtaining means (1) sets the comparison value to 0 if the voxel value at the position of interest is less than or equal to the maximum and greater than or equal to the minimum, (2) sets the comparison value to a difference value between the voxel value and the maximum if the voxel value at the position of interest is greater than the maximum, and (3) sets the comparison value to a difference value between the voxel value and the minimum if the voxel value at the position of interest is less than the minimum.

15. An image processing system comprising:

a memory storing a program; and one or more processors which, by executing the program, function as:

first obtaining means for obtaining a target image constituted by a set of voxels arranged in a discretized manner, wherein each point of the set of voxels constituting the target image is represented with one coordinate;

setting means for setting a search area in the target image, wherein at least one of vertexes of the search area is different from points of the voxels of the target image;

dividing means for dividing the search area into a plurality of partial areas on the basis of positions of points of the voxels of the target image, wherein at least some of the partial areas include at least one of the points of the voxels of the target image as a respective vertex, and wherein at least some of the partial areas respectively include at least one vertex that is not one of the points of the voxels;

interpolating means for generating an interpolated value, wherein generating the interpolated value includes interpolating a voxel value of the target image at a position of a vertex of the vertexes of the plurality of partial areas, wherein the vertex is not any of the points of the voxels; and second obtaining means for obtaining, on the basis of the interpolated value and a voxel value of a voxel having one of the points that is one of the vertexes of at least one of the plurality of partial areas, at least one of (i) a maximum of a voxel value and an interpolated value within the search area and (ii) a minimum of a voxel value and an interpolated value within the search area.

16. An image processing method comprising:

obtaining a target image constituted by a set of voxels arranged in a discretized manner, wherein each point of the set of voxels constituting the target image is represented with one coordinate;

setting a search area in the target image, wherein at least one of vertexes of the search area is different from points of the voxels of the target image;

dividing the search area into a plurality of partial areas on the basis of positions of points of the voxels of the target image, wherein at least some of the partial areas include at least one of the points of the voxels of the target image as a respective vertex, and wherein at least some of the partial areas respectively include at least one vertex that is not one of the points of the voxels;

generating an interpolated value, wherein generating the interpolated value includes interpolating a voxel value of the target image at a position of a vertex of the vertexes of the plurality of partial areas, wherein the vertex is not any of the points of the voxels; and obtaining, on the basis of the interpolated value and a voxel value of a voxel having one of the points that is one of the vertexes of at least one of the plurality of partial areas, at least one of (i) a maximum of a voxel value and an interpolated value within the search area and (ii) a minimum of a voxel value and an interpolated value within the search area.

17. A non-transitory storage medium storing a program causing a computer to perform the image processing method according to claim 16.

* * * * *